US006993175B2

(12) United States Patent
Samoszuk et al.

(10) Patent No.: US 6,993,175 B2
(45) Date of Patent: Jan. 31, 2006

(54) METHODS FOR MEASURING MICROVASCULAR DENSITY IN TUMORS

(75) Inventors: Michael Samoszuk, Rancho Santa Margarita, CA (US); Froilan Espinoza, Mission Viejo, CA (US); Leonard Leonor, Dana Point, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 712 days.

(21) Appl. No.: 09/949,292

(22) Filed: Sep. 7, 2001

(65) Prior Publication Data

US 2003/0050553 A1 Mar. 13, 2003

(51) Int. Cl.
*G06K 9/00* (2006.01)
(52) U.S. Cl. ...................... 382/133; 128/922
(58) Field of Classification Search ................ 382/133, 382/128, 134, 162, 163–165, 206, 190, 192; 356/39; 128/922; 435/1.1
See application file for complete search history.

(56) References Cited

U.S. PATENT DOCUMENTS 5,357,550 A * 10/1994 Asahina et al. ............ 378/98.5
5,616,469 A * 4/1997 Brawer ...................... 435/7.23

OTHER PUBLICATIONS

Cheng, Wen-Fang; Vasculartiy Index as a Novel Parameter for the in Vivo Assessment of Angiogenesis in Patients with Cervical Carcinoma; Cancer; vol. 85, Issue 3, Feb. 1, 1999; pp.: 651-657.*
Kay, Paul; Prostate cancer microvessels: a novel method for three-dimensional reconstruction and analysis; The Prostate; vol. 37; Issue 4; Date: Dec. 1, 1998; pp.: 270-277.*
Abdulkadir, et al, "Tissue Factor Expression and Angiogenesis in Human Prostate Carcinoma," Human Pathology, 31(4):443-447, 2000.
Akslen, et al., "Increased Angiogenesis in Papillary Thyroid Carcinoma but Lack of Prognostic Importance," Human Pathology, 31:439-442, 2000.
Costello, et al., "Prognostic Significance of Microvessel Density in Lymph Node Negative Breast Carcinoma," Human Pathology, 26(11):1181-1184, 1995.
Cruz, et al., "Microvessel Density Counting in Breast Cancer," Analytical and Quantitative Cytology and Histology, 23:15-20, 2001.
Brasch, et al., "MRI Characterization of Tumors and Grading Angiogenesis Using Macromolecular Contrast Media: Status Report," European Journal of Radiology, 34: 148-155, 2000.
de la Taille, et al., "Microvessel Density as a Predictor of PSA Recurrence After Radical Prostatectomy," American Society of Clinical Pathologists, 113: 555-562, 2000.

(Continued)

*Primary Examiner*—Brian Werner
*Assistant Examiner*—Christopher Lavin
(74) *Attorney, Agent, or Firm*—Foley & Lardner LLP

(57) ABSTRACT

The present invention provides methods of determining the microvascular density of tumors. The methods generally comprise creating a digital image of a defined cross section of the tumor, determining the cross-sectional surface area of vascular tissue in the section of the tumor, determining the total cross sectional area of the section of the tumor, calculating the ratio of the cross sectional surface area of the tumor to the total cross sectional area of the section of the tumor, and thereby determining the microvascular density of the tumor. The digital image of the tumor may preferably be created using image processing software and the image may be displayed on a computer screen. The image may be digitally dissected by removing from the image all non-vascular tissue. This approach produces reproducible results that match the results generated by functional MRI assessments of blood perfusion of the tumors.

21 Claims, 2 Drawing Sheets

OTHER PUBLICATIONS

Folberg, et al., "Vasculogenic Mimicry and Tumor Angiogenesis," American Journal of Pathology, 156(2): 361-381, 2000.

Gettman, et al., Role of Microvessel Density in Predicting Recurrence in Pathologic Stage T3 Prostatic Adenocarcinoma, Adult Urology, 54(3): 479-485, 1999.

Graff, et al., "Micromolecule Uptake in Human Melanoma Xenografs: Relationships to Blood Supply, Vascular Density, Microvessel Premeability and Extracellular Volume Fraction," E. J. of Cancer, 36: 1433-1440, 2000.

Jensen, and Chandra, "MR Imaging of Microvasculature," Magnetic Resonance in Medicine, 44: 224-230, 2000.

Locopo, et al., "Assessment of Tumor Vascularization: Immunohistochemical and Non-invasive Methods," Intl. Journal of Biological Markers, 14(4): 218-231, 1999.

McDonald and Foss, "Endothelial Cells of Tumor Vessels: Abnormal but not Absent," Cancer and Metastasis Reviews, 19: 109-120, 2000.

Maniotis, et al., Vascular Channel Formation by Human Melanoma Cells in Vivo and in Vitro: Vasculogenic Mimicry, 155(3): 739-752, 1999.

Medri, et al., "Tumor Microvessel Density and Prognosis in Node-negative Breast Cancer," Intl. Journal of Cancer, 89: 74-80, 2000.

Peters-Engl, et al., "Color-coded and Spectral Doppler Flow in Breast Carcinomas-Relationship with the Tumor Microvasculature," Breast Cancer Research and Treatment, 47: 83-89, 1998.

Samoszuk, et al., "Selective Thrombosis of Tumor Blood Vessels in Mammary Adenocarcinoma Implants in Rats," American Journal of Pathology, 159(1): 245-251, 2001.

Schor, et al., Hetergeneity in Microvascular Density in Lung Tumours: Comparison with Normal Bronchus, British Journal of Cancer, 77(6): 946-951, 1998.

Su, et al., "Tumor Characterization with Dynamic Contrast Enhanced MRI Using MR Contrast Agents of Various Molecular Weights," Magnetic Resonance in Medicine, 39: 259-269, 1998.

Su, et al., "Regional Comparison of Tumor Vascularity and Permeability Parameters Measured by Albumin-Gd-DTPA and Gd-DTPA," Magnetic Resonance in Medicine, 34: 402-411, 1995.

Su, et al., "Characterization of N-Ethyl-N-Nitrosourea-induced Malignant and Benign Breast Tumors in Rats by Using Three MR Contrast Agents," Journal of Magnetic Resonance Imaging, 9:177-186, 1999.

van Dijke, et al., "Mammary Carcinoma Model: Correlation of Macromolecular Contrast-enhanced MR Imaging Characterizations of Tumor Microvasculature and Histologic Capillary Density," Radiology, 198: 813-818, 1996.

Vermeulen, et al., "Quantification of Angiogenesis in Solid Human Tumours: An International Consensus on The Methodology and Criteria of Evaluation," European Journal of Cancer, 32A(14), 2474-2484, 1996.

Weidner, "Current Pathologic Methods for Measuring Intratumoral Microvessel Density within Breast Carcinoma and Other Solid Tumors," Breast Cancer Research and Treatment, 36: 169-180, 1995.

Weidner, "Intratumor Microvessel Density as a Prognostic Factor in Cancer," American Journal of Pathology, 147(1): 9-19, 1995.

* cited by examiner

METHODS FOR MEASURING MICROVASCULAR DENSITY IN TUMORS

INTRODUCTION

The present invention relates generally to the field of tumor evaluation and therapy. In particular, the present invention relates to methods for the convenient, inexpensive, and accurate measurement of the microvascular density of tumors.

BACKGROUND OF THE INVENTION

The following discussion of the background of the invention is merely provided to aid the reader in understanding the invention and is not admitted to describe or constitute prior art to the present invention.

The measurement of microvascular density (MVD) in tumors can provide valuable information to clinicians for evaluating and predicting the biology and clinical behavior of neoplasia. Additionally, MVD is an important variable to consider when evaluating experimental new treatments that target angiogenesis. For example, intratumoral MVD has been proposed as a prognostic factor in various types of cancer and as a marker for treatments that target blood vessels in cancer (Weidner, 1995a, b). Because angiogenesis is typically heterogeneous throughout tumors, it is often difficult to assess overall MVD by manually counting blood vessels in only a few selected portions of tumors (Costello et al, 1995). This difficulty in measuring MVD may be responsible for the various conflicting reports regarding the clinical significance of MVD in breast cancer (Medri et al, 2000), prostate cancer (Gettman et al, 1999; Abdulkadir et al, 2000) and thyroid cancer (Akslen and Livolsi, 2000).

Presently, MRI (magnetic resonance imaging) is a preferred functional assay for assessing blood vessel density within tumors (van Dijke et al., 1996; Brasch and Turetschek, 2000; Jensen and Chandra, 2000). The signal enhancement that is measured by MRI is a function of many variables that confound a simple determination of MVD, including the size of the contrast agent employed, the relative perfusion of the tumor, and the microvascular permeability within the tumor (Su, Muehler et al, 1998) For example, it is important to use a blood pool contrast agent that remains in the vasculature rather than a small contrast agent that quickly leaks into the interstitial space.

Other methods for assessing the functional status of tumor microvasculature include color-coded Doppler flow measurement (Peters-Engl C et al, 1998), positron emission tomography (Fanelli M et al, 1999), and uptake of albumin-Evan's blue dye (Graff et al, 2000). Recently, a number of histochemical methods have also been described for measuring intratumoral MVD. One method involves assessment of neovascular "hot spots" as highlighted with anti-factor VIII antibody (Weidner, 1995b). Other studies suggest that CD31 or CD34 might serve as markers for identifying blood vessels in tumors (Vermeulen et al, 1996; de la Taille et al, 2000). More recently, digital image analysis of breast cancer sections stained with monoclonal antibody to factor VIII has been proposed as a procedure for MVD assessment (Cruz et al, 2001).

There remains a need in the art for convenient, inexpensive, and accurate methods to measure microvascular density in tumors.

SUMMARY OF THE INVENTION

The present invention provides methods for determining the microvascular density of tumors. The methods generally comprise creating a digital image of a defined cross section of the tumor, determining the area of vascular tissue in the tumor section, determining the total area of the tumor section, and calculating the ratio of the area of the vascular tissue to the total area of the tumor section. This ratio can accurately represent the microvascular density of the tumor.

The digital image of the tumor may be displayed on a computer screen, and may preferably be manipulated using image processing software to enhance the accuracy of the methods described herein. Thus, in certain embodiments, the image may be digitally dissected by removing from the image some or all of the non-vascular tissue in the image. The computer may then calculate the microvascular density based on the number of pixels that are attributed to the vascular tissue versus total number of pixels attributable to the entire image of the section of the tumor. Surprisingly, this morphometric approach produces reproducible results that match the results generated by far more complicated and expensive functional MRI assessments of blood perfusion of the tumors.

In a first aspect, the present invention provides methods for determining the microvascular density of a tumor by determining a ratio of an area representing vascular tissue in a digital image of a section of the tumor relative to an area representing total tumor tissue in said digital image. This ratio corresponds to the microvascular density of the tumor. Preferably, this method can comprise one or more of the following steps: (1) providing a digital image of a section of the tumor; (2) determining the cross-sectional surface area representing vascular tissue in the digital image; (3) determining the total area representing tumor in the digital image; and (4) determining the ratio of these two area determinations, wherein the ratio corresponds to the microvascular density of the tumor.

The digital image may be displayed on a computer screen or other visible format, preferably using image processing software. In certain embodiments, a color, or range of colors, that represents the color of vascular tissue in the image is chosen, and those pixels exhibiting the color(s) are summed to calculate the area representing vascular and/or total tumor tissue. By "computer screen" is meant any manner of displaying a digital image. Other visible format that may be used to display the image include any type of electronic or light based visualization system, including but not limited to, projection images, pixel-based imaging, high density imaging, and the like.

In preferred embodiments, non-vascular tissue may be deleted from the image before determining the ratio of the cross-sectional surface area of the vascular tissue in the defined section of the tumor to the total cross-sectional surface area of the defined section of the tumor. The non-vascular tissue may consist of one or more of the following tissue types: lymphatic tissue, epithelial tissue, stromal tissue, and necrotic tissue. In these embodiments, a pathologist or other skilled operator can recognize and delete non-vascular tissue having similar color(s) to vascular tissue that may complicate the MVD determination.

In various embodiments, the digital image may be expressed as pixel elements, and may preferably be displayed on a computer screen or other visual representation provided to the operator.

The ratio representing the MVD may be calculated by dividing the number of pixels attributable to the surface area of the vascular tissue in the section of the tumor by the number of pixels attributable to the total surface area of the section of the tumor. The number of pixels attributable to the total surface area of the defined section of the tumor may be at least about 250,000, and more preferably may be greater than 1,000,000. The ratio may be calculated based on a measurements taken from a plurality of defined sections of the tumor, and preferably may be based on two, three, four, five, ten, or more defined sections of the tumor. The present method provides good reproducibility with a coefficient of variation of less than 30%, and more preferably of about 20%.

In preferred embodiments and to enhance viewing and processing of the image, the image may be magnified relative to the image obtainable by viewing the defined section of the tumor with the naked eye. Thus, the digital image may be provided through a camera, including an analog camera or a digital camera. For example a CCD camera attached to a microscope may be used to capture an image.

The sections of the tumor used in the methods described herein may be prepared by embedding and sectioning a tissue specimen that represents all or a portion of the tumor. For example, tissues can be embedded in paraffin (or other wax commonly used for tissue support), with or without dehydration and/or fixation, and then sectioned on a microtome. Alternatively, fresh tissue may be frozen, often in a supporting medium, and subsequently sectioned. These methods of tissue section preservation are well known within the art.

Preferred tumor sections are representative of a tumor in terms of internal structures, including vascular tissue. The skilled artisan will understand that a tumor is a three dimensional object. The dimensions of a section that is truly representative of the tumor can vary, depending on such factors as the overall dimensions of the tumor, necrotic effects in areas within the tumor, etc. Preferably, tumor sections are a cross section of a tumor that corresponds to at least 1% of a plane passing through the tumor. More preferably, tumor sections correspond to at least 5%, 10%, 15%, 20%, 25%, 30%, 50%, 75%, or about 100% of a plane passing through the tumor. The skilled artisan understands the concept of representative sections of a tumor, as, for example, pathologists rely on such representative sections for many diagnostic procedures.

In another aspect, the present invention comprises a computer programmed to determine a microvascular density according to the methods described herein. Such a computer may store a digital image of a tumor in a storage device, such as a magnetic disk drive, and/or may contain enough volatile memory to store the image in memory. The computer also may contain a central processor that performs the microvascular density calculation according to a series of programming steps that determine the cross-sectional surface area representing vascular tissue in the digital image; determining the total area representing tumor in the digital image; and determine the ratio of these two area determinations In another aspect, the present invention comprises determining a diagnosis and/or prognosis for a patient with a tumor by determining the microvascular density of the tumor according to the methods of the present invention, and utilizing the microvascular density of the tumor to determine the prognosis for the patient with the tumor. In a preferred embodiment, a high vascularization level may indicate a negative prognosis and a low vascularization level may indicate a positive prognosis. For example, a high vascularization level may indicate an invasive carcinoma. Or a low vascularization level may indicate a benign fibroadenoma.

In yet another aspect the present invention provides methods of monitoring a treatment regimen by determining the microvascular density of the tumor according to the methods of the present invention, and comparing two such measurements in a patient from tumor samples obtained at two different times. For example, the ability of a treatment regimen, such as administration of a compound or pharmaceutical preparation, to shrink or destroy a tumor by interfering with vascularization may be monitored. In a preferred embodiment the treatment regimen may be designed to shrink or destroy blood vessels in the tumor.

The skilled artisan will understand that such methods may also be used to screen compounds or pharmaceutical preparations for their ability to affect tumor vascularization.

Similarly, the MVD at two different tumor loci in a patient may be compared by determining the microvascular density of the tumor according to the methods of the present invention, and comparing the MVD obtained from each tumor locus.

While the methods described herein can refer to patient samples, the skilled artisan will understand that any tumor sample can be analyzed by the present methods. For example, in a screening assay, tumors in non-human animals (e.g., rats, mice, rabbits, non-human primates, etc.) may be analyzed by the methods described herein.

DETAILED DESCRIPTION OF THE PREFERRED EMBODIMENTS

Figure 1:
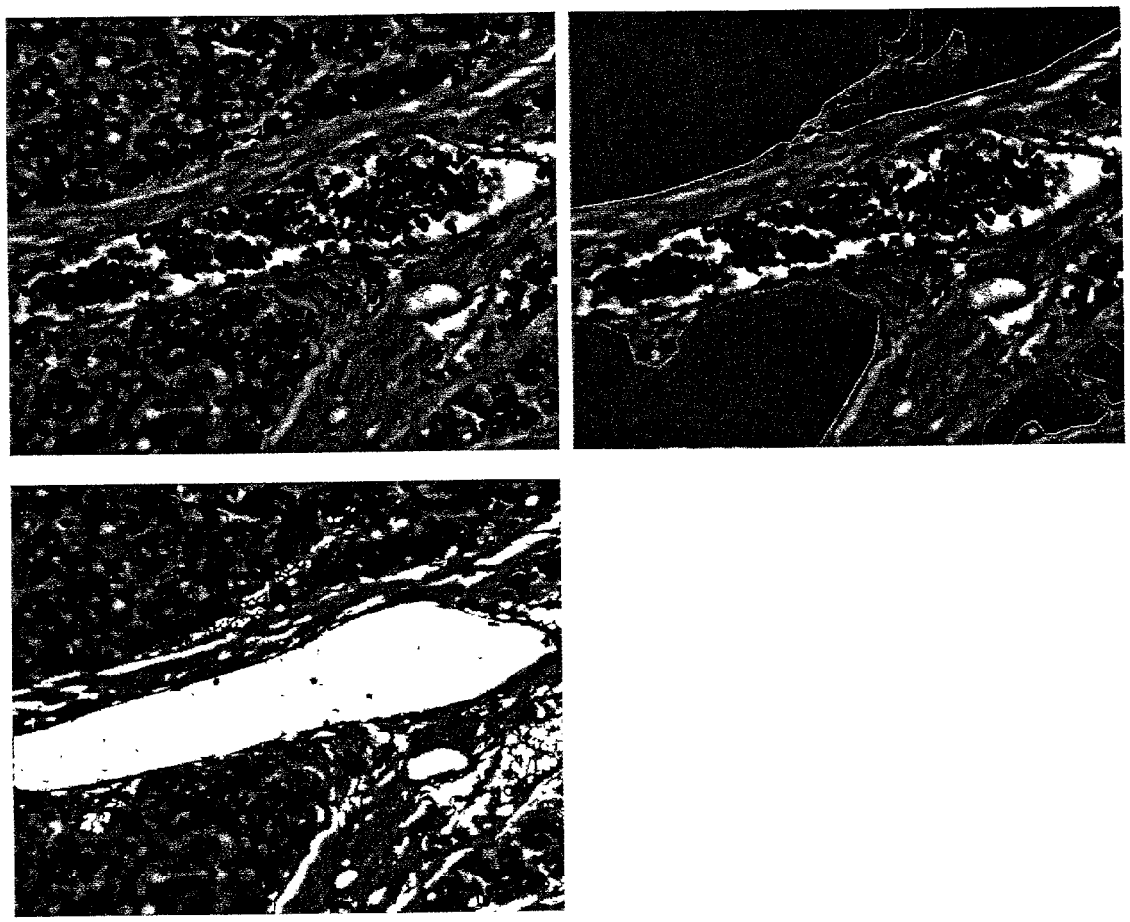
FIG. 1 illustrates a digital dissection of blood vessels in a representative section (top left panel) of a tumor from a rat. The region of interest was selected by manually deleting the portions of the image that were occupied by tumor cells (top right panel). After the red-green-blue values for red blood cells and lumenal spaces were defined by the operator, the software automatically selected and captured the blood vessels within the image (bottom left panel) and counted the number of pixels within the selected region.
Figure 2:
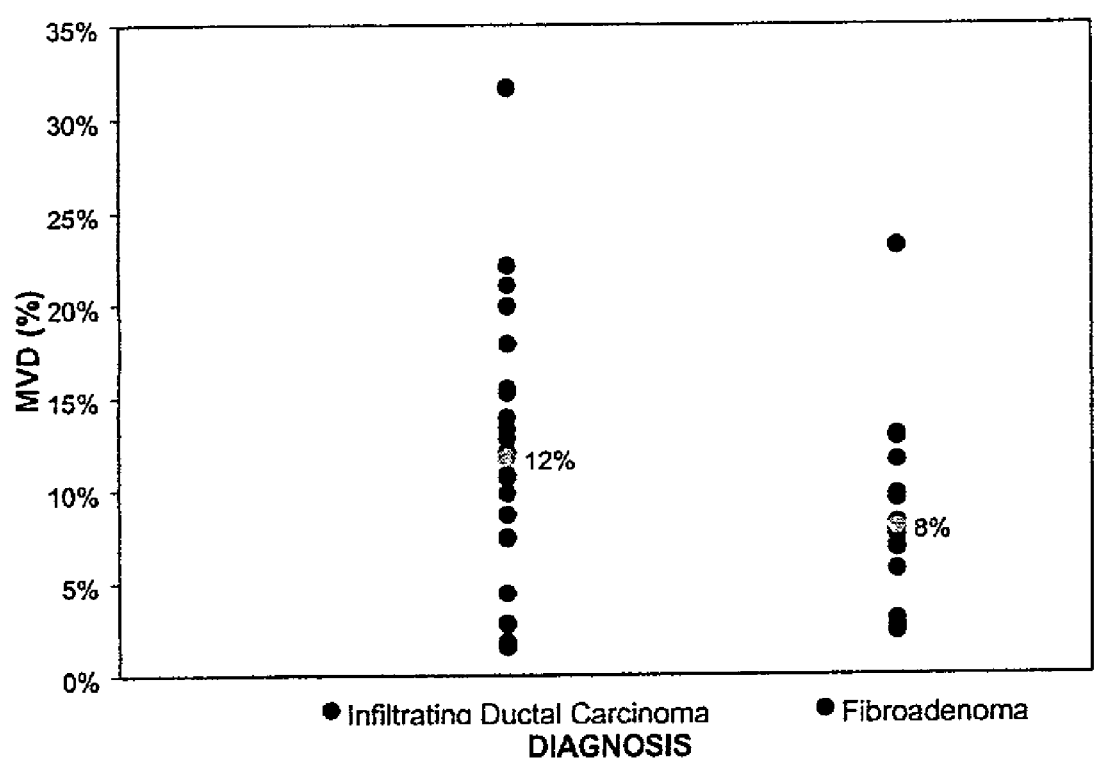
FIG. 2. Illustrates a comparison of MVD results in infiltrating ductal carcinomas and fibroadenomas in rats. The mean MVD of the carcinomas was significantly ($p<0.05$) higher than the mean MVD of the benign fibroadenomas.

The present invention provides a semi-automated procedure for measuring the MVD in tumors. A high degree of precision is attainable with the present methods, and coefficients of variation of less than 20% may easily be achieved. The methods are easily and rapidly performed, often with less than 2 minutes per image being required. The present methods may also be performed at relatively modest cost, thereby reducing diagnostic expenses, particularly in view of the current MRI methods commonly employed. Moreover, unlike MRI, the present methods may be performed on archival specimens, such as biopsy or excised material stored in a pathology laboratory. Furthermore, the present methods do not rely on the immunohistochemical identification of specific vascular endothelial markers or the manual counting of blood vessels, which may not accurately represent the MVD of a sample. Therefore, the present methods can achieve a higher degree of precision and accuracy than past methods at a reduced cost.

Preferably, vascular tissue is identified by a particular characteristic in a digital image. Any characteristic that identifies such tissue in the image can be used. Conveniently, one or more red-green-blue (RGB) values can be identified as representing vascular tissue, based on the color of blood and/or open vascular spaces in the section. Those pixels exhibiting the selected RGB levels can be conveniently summed to arrive at the area in the image embodying vascular tissue. Of course, the particular RGB or other values associated with vascular and other tissue in the image may vary widely dependent on the particular system used. But any characteristic that identifies the tissue by type may be used. The person of ordinary skill will realize that counting pixels is only one way of calculating the area representing tissue, and that pixels need not be used at all. Any means of measuring the area defined by a particular tissue type will function in the present invention. Similarly, while "true color" RGB values can often conveniently be used, "false color" displays of data and texture mapped data, where features displaying a particular characteristic are assigned a color or other distinguishing element for visual display, are also within the scope of the invention.

In those images in which non-vascular tissue is "digitally dissected" and removed from the image before calculating the area representing vasculature or tumor, the skilled operator may identify non-vascular tissue in the image that might interfere in these calculations. For example, non-vascular tissue that exhibits an RGB value similar or identical to that of vasculature can be removed from the image, or its RGB value altered, using an image processing software package. The person of ordinary skill will understand that the particular color combination used to display the image are not important, merely that the colors utilized enable the operator to distinguish one tissue type from another. The person of ordinary skill will also realize that means other than color can be used to distinguish the tissue types, and such means are also contemplated by the present invention.

The measurement of MVD in tumors by any morphometric method is potentially subject to sampling errors due to the intrinsic heterogeneity in the distribution of blood vessels within the tumor (Schor et al, 1998). Thus, the present methods preferably comprise the analysis of multiple images and sections of the tumor in order to gain a more accurate and representative measurement of the overall blood vessel density. Because of the increased speed provided by the automated or semi-automated nature of the methods described herein, the present invention is particularly advantageous when performing such a multi-image analysis. Therefore, the present methods are preferable to manual methods, which are more subject to sampling errors due to the intrinsic heterogeneity in the distribution of blood vessels within the tumor.

The term "microvascular density," or "MVD" as used herein refers to the volume in a tissue sample that is enclosed within the vascular space relative to the total volume of tissue in the sample. The MVD can be expressed as a percentage; i.e., a value of 10% indicates that ten percent of the total volume of a tumor is vascular.

The term "vascular" as used herein refers to a channel within a tissue, organ, human, or animal that conveys blood.

The term "digital image" as used herein refers to a representation (e.g. a "photograph") of an object capable of being stored in digital form. Such images are often referred to in terms of the "depth," or the number of bytes, available for storage of each pixel in the image. An 8-bit image depth refers to an image with 256 possible density levels, while a 16-bit image refers to an image with 65,536 possible density levels. An "RGB" digital image refers to a color image having three different channels, red, green, and blue, each of which has a depth. Shades are created by mixing the relative level of each of these three channels. Thus, an 8-bit RGB value can typically be a set of three values ranging from 0, 0, 0 to 255, 255, 255.

The term "pixel" as used herein refers to a discrete element making up a digital image. Depending on the magnification at which a digital image is recorded, a pixel might represent from about 10 μm to about 1 nm in the original section. This is known to the skilled artisan as the "sampling raster" of the image. In certain aspects, several pixels can be combined, or "binned," to increase the area represented in the resulting binned pixel.

The term "image processing software" refers to a program that is capable of manipulating the elements making up a digital image. Numerous image processing programs are known to the skilled artisan, such as KHOROS, PIKS, GIMP, and IGOR.

A digital image of the tumors to be analyzed may be provided by any suitable means. Persons of ordinary skill in the art are aware of various electronic devices, usually associated with digital cameras or other magnifying devices, that are able to provide a digital image of biological tissue. While the data presented here were generated using specific instrumentation and image analysis software, persons of ordinary skill in the art will realize that equivalent instrumentation and image processing software with the same capabilities is available and known in the art. These instruments and software are also contemplated as embodiments of the present invention. The person of ordinary skill in the art will also realize that the image need not be displayed at all, but may be present within the computer, and analyzed by an automated or other process without being visually presented to the operator. These methods of determining microvascular density are also contemplated in the present invention.

Once obtained, the MVD value can be used for numerous diagnostic, prognostic, and treatment purposes as described herein.

The phrase "diagnosis" as used herein refers to methods by which the skilled artisan can determine whether or not a patient is suffering from a given disease or condition. The skilled artisan often makes a diagnosis on the basis of one or more diagnostic indicators, i.e., a marker, the presence, absence, or amount of which is indicative of the presence or absence of the condition. For example, in the case of various tumors, a given level of vascularization may be associated with and differentiate a malignancy from a benign diagnosis. Thus, MVD may be a diagnostic indicator of certain conditions.

The term "correlating," as used herein in reference to the use of diagnostic indicators, refers to comparing the presence or amount of the diagnostic indicator in a patient to its presence or amount in persons known to suffer from, or known to be at risk of, a given condition; or in persons known to be free of a given condition. In certain embodiments, a threshold level of MVD can be established, and the level of MVD in a patient sample can simply be compared to the threshold level.

The phrase "determining the prognosis" as used herein refers to methods by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. For example, in individuals not exhibiting a given MVD level, the chance of a given outcome may be about 3%. In preferred embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to +/−1%.

The term "positive prognosis" refers to a situation in which the predicted outcome for a particular patient is improved in comparison to an average patient with the same disease. Typical examples of a positive prognosis include a better than average cure rate, a lower propensity for metastasis, a longer than expected life expectancy, differentiation of a benign process from a cancerous process, etc. For example, if a prognosis is that a patient has a 50% probability of being cured of a particular cancer after treatment, while the average patient with the same cancer has only a 25% probability of being cured, then that patient exhibits a positive prognosis. A positive prognosis may be indicated by, for example, chemical destruction of a tumor vasculature. Alternatively, diagnosis of a benign tumor would lead to a positive prognosis if it is distinguished over a cancerous tumor.

Similarly, the term "negative prognosis" refers to a situation in which the predicted outcome for a particular patient is worse in comparison to an average patient with the same disease. Typical examples of a negative prognosis include a worse than average cure rate, an increased propensity for metastasis, a shorter than expected life expectancy, differentiation of a cancerous process from a benign process, etc.

A prognosis is often determined by examining one or more "prognostic indicators." These are markers, such as an MVD level, the presence or amount of which in a patient (or a sample obtained from the patient) signal a probability that a given course or outcome will occur. The skilled artisan will understand that associating a prognostic indicator with a predisposition to an adverse outcome is a statistical analysis. Additionally, a change in marker concentration from baseline levels may be reflective of patient prognosis, and the degree of change in marker level may be related to the severity of adverse events.

Statistical significance is often determined by comparing two or more populations, and determining a confidence interval and/or a p value. See, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. Exemplary statistical tests for associating a prognostic indicator with a predisposition to an adverse outcome are described hereinafter.

Moreover, multiple determinations of MVD can be made, and a temporal change in the marker can be used to determine a diagnosis or prognosis. For example, comparative measurements are made of the MVD of a tumor at multiple time points, and a comparison of two or more MVD values may be indicative of a particular diagnosis or prognosis.

Furthermore, determinations of MVD can be used to assess the ability of a course of treatment to affect a clinical outcome. For example, if a given MVD, or temporal change in MVD is associated with a given outcome, one or more compounds or other treatments can be given to a patient, and their ability to alter the MVD can be assessed. Molecules believed to affect vascularization include interleukin 1, angiostatin, taxol, interferon-α, and various inhibitors of VEGF (vasculoendothelial growth factor) such as PTK787/ZK 222584 or antibodies to VEGF.

EXAMPLE 1

MVD Determination

This example illustrates the digital dissection procedure of the present invention. All tissues were fixed in neutral buffered formalin and embedded into paraffin blocks. Sections of the tumors were cut at 5-micron thickness and then stained with hematoxylin and eosin prior to analysis.

Each tumor was evaluated independently by two pathologists who recorded ten digital images at 40× power from each slide using a Nikon Eclipse E600® (Nikon Corp.) microscope equipped with a Spot® digital camera (Diagnostic Instruments Inc., Sterling Heights, Mich.). A typical slide included two to four different sections of the tumor. Each image represented a randomly selected, non-overlapping region of tumor and connective tissue.

The individual images were digitally dissected and analyzed using the Image-Pro Plus version 4® image analysis software (Media Cybernetics, Silver Spring, Md.). In order to select blood vessels for measurement, additive 3×3 pixel cubes of defined 8-bit (i.e., minimum values of 0 and maximum values of 255 in arbitrary units for each color channel) red-green-blue (RGB) value were utilized. The RGB color values were defined by the color of red blood cells in the image and by the color of the empty space in the blood vessels. Generally each image required at least three cube values for assessment. For red blood cells, the RGB values ranged approximately from 176, 43, 85 to 239, 99, 134. Thus, we defined the criteria for intravascular space measurement as a combination of red blood cells and clear areas devoid of any staining.

These criteria do not necessarily exclude lymphatic vascular channels without red blood cells. But the results indicate that such "lymphatic" channels without red blood cells generally constituted significantly less than 10% of the total MVD in a typical microscopic field. Therefore, no correction was applied to compensate for possible lymphatic vessels.

The majority of the images had a complex histology with epithelial, stromal and vascular components. In certain cases, the RGB values of red blood cell overlapped with necrotic debris, glandular intra-lumenal debris and non-specific stromal components (e.g. collagen, etc.). It was therefore found preferable to have a pathologist subtract digitally those areas consisting primarily of tumor cells and necrosis. Generally, non-vascular tissue such as lymphatic tissue, epithelial tissue, stromal tissue and necrotic tissue were digitally subtracted from the image. The exclusion of these overlapping pixels was easily accomplished using the "area of interest" tool that was incorporated into the software. When set for an "irregular" area, this tool permitted the operator to define an area of any shape within the image to which the RGB values would be applied. Essentially, the tool "digitally dissected" the region of interest away from the extraneous tissues and debris.

After the operator defined the RGB values and the area of interest, the statistical program accompanying the image analysis software then counted the number of pixels with the defined RGB values within the defined area. The average number of pixels corresponding to red blood cells and vessel lumen was then calculated for the 10 representative fields from each tumor. Because there are 1,358,395 pixels in the image array for the Spot® camera, we then calculated the ratio of blood vessel pixels to total pixels in the image. This ratio represented the proportion of the total surface area of the image that was occupied by blood vessels and was a two-dimensional approximation of the MVD. The results were multiplied by a factor of 100 in order to represent the percentage of the area of the image occupied by cross-sections of blood vessels.

While this particular digital camera utilizes 1,358,395 pixels, persons of ordinary skill in the art will realize that a digital image (whether generated by a digital camera or other means) may utilize a different number of pixels. Thus, cameras with at least 250,000 pixels are preferably, and most preferable are cameras with greater than 1,000,000 pixels. Persons of ordinary skill in the art will also realize that the digital image need not utilize pixels at all, but any suitable means of quantifying the area of an image or portion of an image will function in the present invention, and is contemplated as an embodiment of the present invention. Preferably, the ratio is calculated within 5 minutes of determining the cross-sectional surface area of either the vascular tissue in a defined section of a tumor or the total cross-sectional surface area in the defined section of the tumor. Most preferably, the ratio will be calculated in a matter of one minute or even a few seconds or less, because it will be done in an automated fashion and through electronic means.

EXAMPLE 2

Comparison to MRI

This example discusses the correlation of results obtained with the present MVD method with results obtained using MRI (magnetic resonance imaging) methods. It has previously been shown that the peak signal enhancement in dynamic contrast-enhanced MRI is related to vascular density (Su, Najafi et al., 1995). Thus, MRI is accepted by those of skill in the art to represent the most accurate method presently known for estimating MVD.

Four experimental rat tumors were obtained and subjected to dynamic contrast enhanced MRI, and ranked according to blood volume. The MRI measurements of blood volume within the four tumors in rats used for the initial validation studies were performed exactly as described in a previous publication (Samoszuk et al, 2001). In brief, a macromolecular contrast agent (albumin-Gd-DTPA) was injected into the tail vein of the rats, and the time course of signal enhancement was measured in the tumor. The blood volume was determined as the y-intercept by performing linear regression fitting to the last 30 data points (Su, Najafi et al., 1995). The intercept enhancement for each tumor was determined, and the tumors ranked according to blood volume.

An identical rank order was obtained using the MVD methods of the present invention, and the same rank order was again obtained when the present method was repeated with a second pathologist independently performing the digital dissection:

| Tumor | Peak Signal Enhancement (MRI) | MVD (digital dissection) |
|---|---|---|
| A | 16.9 | 3.4% |
| B | 30 | 6% |
| C | 8.3 | 2.6% |
| D | 18.3 | 4% |

Linear regression analysis relating the present MVD method to the MRI results yielded $R^2=0.86$, with an F value of 18.8 and a significance level of 0.049.

EXAMPLE 3

Use as a Diagnostic Tool

The present invention also provides methods for determining a diagnosis or prognosis for a patient with a tumor. The MVD in 40 experimental rat tumors (21 infiltrating ductal carcinomas and 19 benign fibroadenomas) was determined according to the method described in Example 1.

The mean for the invasive carcinomas (11.9%) was significantly higher ($p=0.028$ by a two-sample t-test for the difference in the means of two samples, assuming equal variances) than the mean MVD for the benign fibroadenomas (7.9%). These results are consistent with a previous report that invasive carcinomas generally have a greater blood perfusion than benign fibroadenomas when assessed by MRI (Su et al, 1999).

Therefore, the present invention may also be used to determine a prognosis for a patient based on the microvascular density because the microvascular density is an indication of the type of tumor involved. An invasive ductal carcinoma, which typically has a high level of vascularization, would be associated with a less favorable prognosis. Conversely, a benign fibroadenoma, which typically has a lower level of vascularization, would be associated with a more favorable prognosis.

EXAMPLE 4

Comparison to Factor VIII Immunostaining

The relationship between the present digital MVD determination and MVD estimated by factor VIII staining was analyzed in 10 cases of human breast cancer. Representative sections were immunostained with monoclonal antibody to human factor VIII (Dako, Carpenteria, Calif.) using standard immunohistochemical staining techniques. For each tumor, we then acquired images of five non-overlapping fields. These images were then analyzed with the Image-Pro Plus v. 4® softwareIn brief, the outline of blood vessels that were stained with the factor VIII antibody in each image were manually traced, and the software then used to integrate the area of each image that was enclosed by each continuous tracing. Results were expressed as a percentage of the total surface area of each image.

In every case, the MVD exceeded the area of the tumor that was circumscribed by factor VIII immunostaining. Microscopic examination confirmed that factor VIII did not stain all of the vascular channels that contained red blood cells within the tumors. Moreover, factor VIII staining was frequently discontinuous or faint, making it difficult to trace and measure the surface area bounded by factor VIII.

EXAMPLE 5

Use as a Monitoring Tool

This example provides an illustration of how the present invention may be utilized to monitor a treatment regimen for shrinking or destroying a tumor. A patient is diagnosed with a tumor. A sample of the tumor is taken and analyzed according to the MVD methods of the present invention. Thus, a numerical value is obtained that described the microvascular density of the tumor. The health care professional, utilizing the MVD data and/or other data diagnoses the patient as having an invasive carcinoma. An appropriate treatment regimen is prescribed, and the patient begins the therapy. The therapy is designed to target angiogenesis in the tumor. The therapy will desirably shrink existing blood vessels or inhibit formation of new blood vessels and thereby starve the tumor of nutrients and cause it to shrink and/or be destroyed.

At intervals specified by the health care professional a sample of the tumor is again taken from the patient, and analyzed according to the MVD methods of the present invention. The ratio obtained may be compared to the ratio obtained from the initial tumor sample. The health care professional is able to monitor the effectiveness of the therapy at very modest cost by gathering data about the microvascular density of the tumor. If the microvascular density of the tumor declines, it is an indication that the therapy is having the desired effect. Conversely, if the microvascular density increases or remains unchanged, other therapies may be tried.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for determining the microvascular density of a tumor comprising:
   obtaining using a camera a digital image of a section cut from a tumor;
   identifying vascular tissue and tumor in a section of the digital image wherein said vascular tissue is not identified by detection of specific vascular endothelial markers;
   determining a ratio of an area representing vascular tissue in said section of the digital image of the tumor relative to an area representing total tumor tissue in said section of the digital image of the tumor, wherein said ratio corresponds to the microvascular density of the tumor.

2. The method of claim 1 wherein the ratio is determined by
   (a) determining the area representing vascular tissue in said digital image;
   (b) determining the area representing total tumor tissue in said digital image; and
   (c) calculating said ratio by dividing the area from step a by the area from step b.

3. The method of claim 1 or 2 wherein the digital image is displayed on a computer screen and manipulated using image processing software.

4. The method of claim 1 or 2 wherein the area representing vascular tissue and the total area are cross-sectional surface areas.

5. The method of claim 1 or 2 wherein non-vascular tissue is deleted from the image before determining said ratio.

6. The method of claim 5 wherein the non-vascular tissue consists of one or more of the following tissue types: lymphatic tissue, epithelial tissue, stromal tissue, glandular tissue, and necrotic tissue.

7. The method of claim 1 or 2 wherein the ratio is calculated by dividing the number of pixels attributable to the area representing vascular tissue by the number of pixels attributable to the total tumor tissue in said digital image.

8. The method of claim 6 wherein the pixels attributable to the area representing vascular tissue are identified by selecting those pixels having one or more selected RGB values.

9. The method of claim 1 wherein the coefficient of variation of the method is less than 30%.

10. The method of claim 9 wherein the ratio is calculated based on at least three sections of the tumor.

11. The method of claim 1 wherein the ratio is calculated based on a plurality of sections of the tumor.

12. The method of claim 1 wherein said camera is a digital camera.

13. The method of claim 12 wherein the image of the section of the tumor is magnified about 40×.

14. The method of claim 1 wherein the digital image of the section of the tumor is magnified relative to the image of the section of the tumor observable by the unaided eye.

15. The method of claim 1 wherein the section of the tumor is obtained by embedding all or a portion of the tumor in paraffin and sectioning the embedded tumor.

16. A method for monitoring a treatment regimen in a patient with a tumor comprising:

determining the microvascular density of the tumor according to the method of claim 1; and;

comparing the microvascular density to a pre-treatment microvascular density value; and determining the effectiveness of the treatment regimen in shrinking or destroying the tumor.

17. The method of claim 16 wherein the treatment regimen is designed to shrink or destroy blood vessels in the tumor.

18. The method of claim 1 or 2 wherein said vascular tissue and tumor tissue are identified by color.

19. The method of claim 18 wherein said color results from staining the tissue section.

20. The method of claim 19 wherein said staining is with hematoxylin and eosin.

21. The method of claim 1 wherein said vascular tissue is identified by the presence of red blood cells.

* * * * *